United States Patent [19]

Taniguchi et al.

[11] Patent Number: 4,675,307

[45] Date of Patent: Jun. 23, 1987

[54] ALKALI METAL-SUPPORTED CATALYST

[75] Inventors: Katsuo Taniguchi, Iwakuni; Tadaaki Fujimoto, Yamaguchi; Kenji Saeki, Ohtake, all of Japan

[73] Assignee: Mitsui Petrochemical Industries, Ltd., Tokyo, Japan

[21] Appl. No.: 826,489

[22] PCT Filed: May 28, 1985

[86] PCT No.: PCT/JP85/00291

§ 371 Date: Jan. 23, 1986

§ 102(e) Date: Jan. 23, 1986

[87] PCT Pub. No.: WO85/05562

PCT Pub. Date: Dec. 19, 1985

[30] Foreign Application Priority Data

May 28, 1984 [JP] Japan .................................. 59-108130
Jun. 18, 1984 [JP] Japan .................................. 59-123660

[51] Int. Cl.$^4$ ........................ B01J 21/04; B01J 23/02; B01J 23/26; B01J 23/78

[52] U.S. Cl. ..................................... 502/306; 502/328; 502/341

[58] Field of Search ........................ 502/306, 328, 341

[56] References Cited

U.S. PATENT DOCUMENTS 3,577,354  5/1971  Kehl .................................. 502/306

FOREIGN PATENT DOCUMENTS 95783  12/1983  European Pat. Off. ............ 502/328
49-3760  1/1974  Japan .
55-69525  5/1980  Japan .................................. 502/306

Primary Examiner—W. J. Shine
Attorney, Agent, or Firm—Sherman and Shalloway

[57] ABSTRACT

An alkali metal-supported substance comprising a calcination product of a hydrotalcite-like compound having Mg as a divalent metal and a carbonate ion as an anion and an alkali metal supported on the calcination product. When this substance is treated with a gas containing molecular oxygen, part of the alkali metal is converted to its oxide to give a more stable substance. These substances act, for example, as an isomerization catalyst for olefins.

12 Claims, 2 Drawing Figures

ALKALI METAL-SUPPORTED CATALYST

TECHNOLOGICAL FIELD

This invention relates to an alkali metal-supported substance which particularly is useful as an isomerization reaction catalyst.

BACKGROUND TECHNOLOGY

One known strongly basic catalyst used, for example, in the isomerization of olefins is an alkali metal-supported substance prepared by depositing an alkali metal on a carrier having a high specific surface area such as active alumina (see Japanese Patent Publication No. 24138/1970). This substance has high catalytic activity but is very unstable, and even when meticulous cares are taken in its preparation, storage, operational treatments, etc., it cannot show stable catalytic performance.

DISCLOSURE OF THE INVENTION

It is an object of this invention to provide a novel alkali metal-supported substance by a novel combination of a carrier substance and a substance to be deposited.

Another object of this invention is to provide an active alkali metal-supported substance having high activity as a strongly basic catalyst.

Still another object of this invention is to provide an alkali metal-supported substance which can be prepared with good reproducibility and therefore can exhibit highly active catalytic ability with good reproducibility.

Yet another object of this invention is to provide a stabilized alkali metal-supported substance which is not likely to ignite even on contact with water, compounds containing water, or moist air and is easy to handle.

A further object of this invention is to provide a highly active and strongly basic solid catalyst useful, for example, as an isomerization catalyst for olefins.

Still further object of this invention is to provide a method for isomerizing olefins using the substance of this invention as an isomerization catalyst.

Other objects and advantages of this invention will become apparent from the following description.

According to this invention, these objects and advantages of the invention are achieved by an alkali metal-supported substance comprising a calcination product of a hydrotalcite compound represented by the following formula (I)

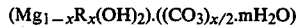

wherein R is Al, Cr or Fe, x is a number represented by $0<x<0.34$, and m is a number represented by $0<m<5$, and an alkali metal supported on the calcination product.

BEST MODE FOR PRACTICING THE INVENTION AND ITS INDUSTRIAL UTILIZABILITY

Figure 1:
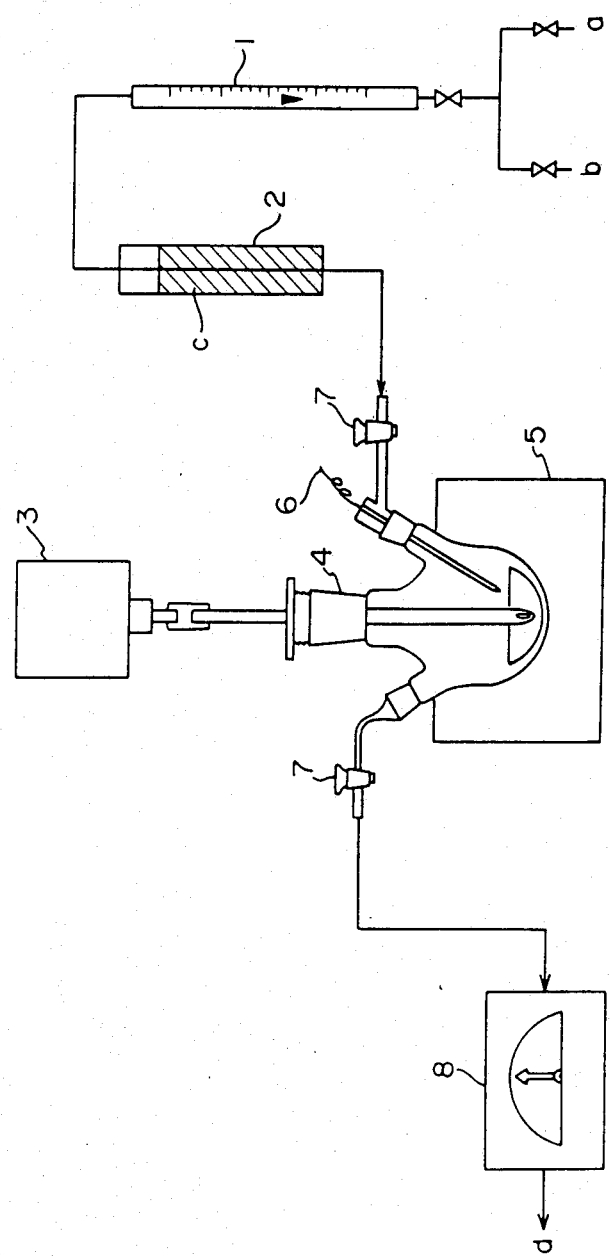
FIG. 1 of the accompanying drawings shows one example of a laboratory-scale device for treating an alkali metal-supported substance.

The hydrotalcite compounds of formula (I) constitute part of hydrotalcite compounds represented by the following formula (II)

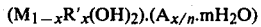

wherein M is a divalent metal, R' is a trivalent metal, A is an anion having a valence of n, n is 1 or 2, and x and m are as defined in formula (I) above.

The hydrotalcite compounds of formula (II) include those in which M is a divalent metal such as Mg, Zn, Mn and Ni, R' is a trivalent metal such as Al, Cr or Fe, and A is an inorganic anion such as $F^-$, $Cl^-$, $Br^-$, $I^-$, $CO_3^{2-}$, $CrO_4^{2-}$, $HPO_4^{2-}$, $NO_3^-$, $SO_4^{2-}$ or an organic anion such as an oxalate or salicylate anion. The above hydrotalcite compounds of formula (I) correspond to compounds of formula (II) in which M is Mg, R' is Al, Cr or Fe and A is $CO_3^{2-}$.

The hydrotalcite compounds of general formula (I) have a crystal structure in which the structural matrix consists of basic layers formed by the combination of octahedrons having Mg as a central metal ion in a network pattern and since these basic layers are positively charged by partial replacement of Mg therein with the metal R, ion-exchangeable $CO_3$ anions are present between these basic layers to maintain a neutral charge. Water is also present between these basic layers.

Examples of the hydrotalcite compounds of formula (I) are
$[Mg_{0.75}Al_{0.25}(OH)_2] \cdot [(CO_3)_{1/8}0.0.5-0.652H_2O]$,
$[Mg_{9/13}Al_{4/13}(OH)_2] \cdot [(CO_3)_{2/13} \cdot 7/13H_2O]$,
$[Mg_{2/3}Al_{1/3}(OH)_2] \cdot [(CO_3)_{1/6} \cdot 0.5H_2O]$,
$[Mg_{2/3}Fe_{1/3}(OH)_2] \cdot [(CO_3)_{1/6} \cdot mH_2O]$, and
$[Mg_{2/3}Cr_{1/3}(OH)_2] \cdot [(CO_3)_{1/6}mH_2O]$.

These compounds, in the order stated, may also be written as follows:
$Mg_6Al_2(OH)_{16}CO_3 \cdot 4-5H_2O$,
$Mg_{4.5}Al_2(OH)_{13}CO_3 \cdot 3.5H_2O$,
$Mg_4Al_2(OH)_{12}CO \cdot 3H_2O$,
$Mg_4Fe_2(OH)_{12}CO_3 \cdot 6mH_2O$, and
$Mg_4Cr_2(OH)_{12}CO \cdot 6mH_2O$.

Of the above hydrotalcite compounds, those of formula (I) in which R is Al are especially preferably used. These hydrotalcite compounds are used in the form of a calcination product in the present invention.

Calcination of the hydrotalcite compounds is carried out generally at a temperature of about 300° to 700° C., preferably about 400° to 600° C., for at least 1 hour, preferably for 1 to 5 hours. Desirably, the calcination treatment is carried out in nitrogen gas or dry air, preferably in a stream of nitrogen gas.

The calcination product used in this invention has such a sufficient basic strength that usually when diphenylamine as an indicator is adsorbed on it, the color of the indicator changes from an acidic color (colorless) to a basic color (pale blue), namely a pKa higher than 22.3. The calcination product of such a high base strength can be obtained by calcining a hydrotalcite compound of general formula (II) in which the divalent metal is magnesium, above all the hydrotalcite compound of general formula (I).

The hydrotalcite compound or its calcination product generally has a specific surface area of as high as at least 100 m²/g, whereas a basic carrier, such as magnesium oxide, used in known alkali metal-supported substances has a specific surface area of about 20 m²/g.

Investigations of the present inventors have shown that when an alkali metal is supported on the above calcination product, it is dispersed highly to form a highly active stable strongly basic solid catalyst. Particularly, it has been made clear that when an alkali metal is supported on a calcination product of the strongly basic hydrotalcite compound of general formula (I) as a carrier, a very highly active catalyst is obtained.

Deposition of the alkali metal on the calcination product carrier may be effected, for example, by a method comprising heating a lump of the alkali metal to a temperature above its melting point, and adding it with good stirring to the carrier in the form of a powder or granules or in a molded form, or by a method comprising vapor depositing the alkali metal on the carrier under reduced pressure.

The amount of the alkali metal deposited on the carrier is preferably about 1 to 15% by weight, more preferably about 3 to 10% by weight, based on the weight of the carrier. If the amount is smaller than the above-mentioned, the desired catalytic activity is difficult to obtain. If it is used in a larger amount, the dispersion of the alkali metal tends to become poor.

The alkali metal to be supported is, for example, lithium, sodium, potassium, rubidium or cesium. Generally, sodium is preferred.

The X-ray powder diffraction pattern (measured in a nitrogen atmosphere) of the resulting alkali metal-supported substance shows no peak assignable to the alkali metal. When, for example, this alkali metal-supported substance is treated with water, hydrogen gas is evolved. It is seen from this that the alkali metal deposited is finely dispersed as a metal on the carrier.

The known alkali metal-supported substance composed of a metal oxide such as alumina and an alkali metal deposited thereon shows no peak attributed to the alkali metal by X-ray analysis. Neither does the alkali metal-supported substance of this invention.

The alkali metal-supported substance of this invention shows high activity as a strongly basic solid catalyst, for example in the isomerization reaction of olefins, dehydrogenation reaction, hydrogenation reaction, oligomerization reaction and addition reaction and various condensation reactions. Particularly, it shows an excellent catalytic action on the isomerization of olefins, and is particularly effective, for example, for the isomerization of an alkenyl crosslinked cyclic compound to an alkylidene crosslinked cyclic compound and the double bond immigration reaction of unsaturated aliphatic hydrocarbons.

Investigations of the present inventors have also shown that when the alkali metal-supported substance is treated with a gas containing molecular oxygen, the supported substance reacts with water to give a product which has no danger of inflammation, is easy and convenient to handle, and maintains high catalytic activity.

In the present invention, the treatment of the alkali metal-supported substance is carried out, for example, as follows. A water-free dry gas obtained by diluting oxygen with an inert gas such as nitrogen, helium or argon is used in this invention as the oxygen-containing gas. The oxygen concentration is 3 to 30% by volume. Usually, dry air or air diluted with nitrogen is used. In particular, a gaseous mixture having an oxygen concentration of 5 to 10% is preferred because it makes the stabilization operation easy. In the above method, the treatment of the alkali metal-supported substance with the oxygen-containing gas is carried out usually at a temperature of 25° to 200° C., preferably 50° to 150° C. The treatment in this case is carried out usually by passing the oxygen-containing gas in portions of a proper amount into a container containing the alkali metal-supported substance, or by sealing a gas containing the required amount of oxygen into a container together with the alkali metal-supported substance. Stabilization temperatures lower than 25° C. are undesirable because the reaction of the alkali metal with oxygen becomes extremely slow. Even when, for example, a period of several tens of hours is spent, the stabilization treatment greatly tends to become insufficient. When the stabilization treatment is carried out at temperatures higher than 200° C., the resulting alkali metal-supported substance has reduced activity in the various reactions stated above, above all in the isomerization of olefins. The time required for the stabilization treatment in accordance with this invention differs slightly depending upon the temperature and oxygen concentration used, but is usually about 10 to about 120 minutes. If the treating time becomes shorter than the specified limit, it is not rare that the alkali metal-supported substance shows inflammability. If the treating time becomes longer than the specified limit, the activity of the alkali metal-deposited substance as a catalyst for the various reactions stated above is undesirably reduced.

By employing the aforesaid method of stabilization treatment which is a simple treatment never tried heretofore, there can be obtained a stabilized alkali metal-supported substance which even when contacted with water, does not ignite by the evolution of hydrogen, and which is very safe and easy to handle. When the alkali metal in the alkali metal-supported substance is sodium, hydrogen is generated in accordance with the following reaction.

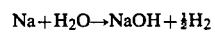

In the stabilized alkali metal-supported substance of this invention, however, part of the alkali metal is converted to an alkali metal compound such as an oxide by the treatment with the oxygen-containing gas and supported as such. Hence, the amount of hydrogen generated upon contact with water is very small and usually this amount is less than about 15%, for example, of the theoretical amount of hydrogen generated when it is assumed that the alkali metal compound in the amount calculated as alkali metal, i.e. the entire amount of the alkali metal deposited on the carrier before treatment with the oxygen-containing gas, reacts with water to form a hydroxide. For this reason, the resulting stabilized alkali metal-supported substance is free from a danger of inflammation and very safe and easy to handle.

Since the stabilized alkali metal-supported substance has superstrong basicity shown by a pKa value of at least 35.0, it can be used as a strongly basic solid catalyst. The pKa value of 35.0 showing basic strength is the strongest base strength which can be measured by the presently known indicator measuring method. This also means that in the temperature programmed desorption method, benzoic acid molecules exist which are still adsorbed on the catalyst even at 350° C.

The aforesaid method of stabilization treatment of the supported substance is applicable not only to alkali metal-supported substances obtained by supporting alkali metals on a calcination product of the aforesaid hydrotalcite compound, but also directly to alkali metal-supported substances obtained by depositing 1 to 15% by weight, based on the weight of the carrier to be described, of an alkali metal compound as alkali metal on at least one carrier selected from alkaline earth metal oxides such as MgO, CaO, SrO and BaO, rare earth oxides such as $La_2O_3$, $CeO_2$ and $Y_2O_3$, metal oxides such as alumina, silica, silica-alumina, thorium oxide, zirconium oxide, zinc oxide, titanium dioxide, talc, diatomaceous earth, Celite, bentonite and zeolite, metal salts such as potassium carbonate, sodium carbonate, magnesium carbonate and potassium borate and carbonaceous materials such as silicon carbide, graphite and activated carbon. This stabilization treatment can give a stabilized alkali metal-supported substance having the following characteristics:

(A) it has a maximum basic strength, in pKa, of at least 35, and (B) the amount of hydrogen gas generated by reaction with water is less than, for example, 15% of the theoretical amount of hydrogen generated when it is assumed that if the alkali metal compound contained in the above substance is calculated as the alkali metal, the entire amount of the alkali metal is reacted with water in accordance with the following formula:

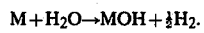
$M+H_2O \rightarrow MOH + \frac{1}{2}H_2$.

The alkali metal-supported substance or the stabilized alkali metal-supported substance in accordance with this invention is suitably used as a strongly basic solid catalyst in the various reactions stated above.

Examples of the olefins to be isomerized by using the aforesaid substance as a catalyst include straight-chain or branched-chain unsaturated chain aliphatic hydrocarbons such as butene, pentene, methylpentene, dimethylbutene, hexene, heptene, octene, nonene and decene; unsaturated alicyclic hydrocarbons such as methylcyclopentene, ethylcyclopentene, methylcyclohexene, ethylcyclohexene and vinyl cyclohexene; alkenyl cyclic hydrocarbons such as vinylcyclohexene and allylcyclohexene; alkenyl crosslinked cyclic compounds such as alkenyl vinycloheptenes; unsaturated amine compounds such as allylamine, butenylamine and pyrroline; and unsaturated ether compounds such as ethyl crotyl ether, 6-methoxy-1-hexene and 3-methoxy-1-butene.

The isomerization reaction of the unsaturated chain aliphatic hydrocarbons includes skeletal isomerization reaction and double bond immigration reaction. For example, when butene-1 is used, cis-butene-2 and trans-butene-2 are obtained as main components. When 4-methyl-pentene-1 is used, cis-4-methylpentene-2, trans-4-methylpentene-2, 2-methylpentene-1, 2-methylpentene-2 and 3-methylpentene-2 are obtained as products. When 3-methylpentene-1 is used, cis-3-methylpentene-2 and trans-3-methylpentene-2 are obtained as products. From octene-1, octene-2, octene-3 and octene-4 are obtained as products.

When such an isomerization reaction gives two or more reaction products, it is possible to form a particular isomerization product selectively to some extent by, for example, properly selecting the reaction temperature, the reaction time, etc. The unsaturated chain aliphatic hydrocarbons having an internal double bond which are obtained by this isomerization reaction are useful as starting materials for the production of secondary alcohols by hydration, or starting materials for the disproportionation of olefins.

In the isomerization of the alkenyl bicycloheptenes, 5-ethylidene-2-norbornene is obtained as a product from 5-vinyl-2-norbornene; 5-propylidene-2-norbornene is obtained as a product from 5-propenyl-2-norbornene; and 5-isopropylidene-2-norbornene is obtained as a reaction product from 5-isopropenyl-2-norbornene. These 5-alkylidene-2-norbornenes are monomers which are important, for example, as the diene component of EPDM.

In the isomerization of olefins, the strongly basic solid catalyst which is the alkali metal-supported substance or the stabilized alkali metal-supported substance is used generally in a proportion of about 0.001 to 1 g-atom, preferably about 0.01 to 0.1 g-atom, as the alkali metal, per mole of the starting olefin.

The isomerization reaction is generally carried out in the absence of a solvent. It may be carried out in a solvent which does not obstruct the reaction. Usable solvents include hydrocarbons, for example aliphatic, alicyclic or aromatic hydrocarbons having 5 to 20 carbon atoms, such as pentane, hexane, heptane, octane, dodecane, cyclohexane, benzene, toluene and xylene; and ethers such as diethyl ether, dibutyl ether, ethylene glycol dimethyl ether, diethylene glycol dimethyl ether, tetrahydrofuran and tetrahydropyran.

The conditions used in the reaction include atmospheric or elevated pressures, for example 0 to 5 kg/cm²-G and temperatures of about 0° to 120° C., preferably about 20° to 100° C. The reaction may be operated by any one of the batch method, semi-continuous method and continuous method.

The alkali metal-supported substance and the stabilized alkali metal-supported substance in accordance with this invention can be used effectively not only as an isomerization reaction catalyst for olefins, but also as catalysts for dehydrogenation reaction, hydrogenation reaction, oligomerization, addition-reaction and various condensation reactions.

The dehydrogenation may, for example, be the dehydrogenation of olefins to obtain diene compounds, such as the reaction of obtaining isoprene from 2-methyl-1-butene and 2-methyl-2-butene, the reaction of obtaining 2,3-dimethyl-1,3-butadiene from 2,3-dimethyl-1-butene and 2,3-dimethyl-2-butene, the reaction of obtaining butadiene from butene-1 and butene-2, and the reaction of obtaining piperylene from pentene.

The oligomerization reaction may, for example, be the reaction of butadiene or isoprene to form an oligomer. The addition-reaction may, for example, be the reaction of adding a chain aliphatic unsaturated hydrocarbon having 2 to 5 carbon atoms to an alkyl-substituted benzene such as toluene, ethylbenzene, xylene or isopropylbenzene, or the reaction of an amino compound such as diethylamine with a conjugated diene such as butadiene to form, for example, 2-butenyl diethylamine.

The following examples illustrate the present invention further.

EXAMPLE 1

(1) As a hydrotalcite compound, $Mg_{4.5}Al_2(OH)_{13}CO_3.3.5H_2O$ (Kyoward #1000, a tradename for a product of Kyowa Chemical Co., Ltd.) was used.

Five hundred grams of this compound was calcined in air at 500° C. for 3 hours. The calcination product had a specific surface area, measured by a B.E.T. one-point method in a Quantasorb specific surface area measuring device made by Quantachrome Company, of 174 m²/g. The specific surface area markedly increased from its original value of 121 m²/g before the calcination. When the basic strength of the calcination product was measured by an indicator measuring method, 4-chloroaniline having a pKa of 26.5 turned pink from its colorless state, and the product showed high basicity.

One hundred grams of the calcination product in powder form was taken into a flask, and heated to 250° C. in an atmosphere of nitrogen gas. With good stirring, 8.7 g of metallic sodium was added in small portions over the course of about 20 minutes, and the mixture was stirred for about 2 hours to deposit 8.0% by weight of metallic sodium on the powdery calcination product of the hydrotalcite compound. When the basic strength of the resulting substance was measured by the indicator titration method, triphenylmethane having a pKa of 35.0 turned yellow from its colorless state, and the substance showed superstrong basicity.

(2) Two grams of the resulting sodium-supported substance was put in a flask charged with 250 g of 5-vinyl-2-norbornene, and the mixture was stirred for 60 minutes at 80° C. under atmospheric pressure. When the reaction mixture was analyzed by gas chromatography (PEG 20 M, 3 m), it was found that all the 5-vinyl-2-norbornene changed to 5-ethylidene-2-norbornene, and the presence of by-products was not observed.

EXAMPLE 2

(1) In the same way as in Example 1, a substance having metallic sodium deposited in an amount of 9.0% by weight was obtained except that $Mg_6Al_2(OH)_{16}CO_3.4H_2O$ (Kyoward #500, a tradename for a product of Kyowa Chemical Co., Ltd.) was used as the hydrotalcite compound, 9.8 g of metallic sodium was used and that the hydrotalcite-like compound was calcined at 550° C.

The specific surface area of the hydrotalcite compound, measured after calcination by the same method as described in Example 1, was 163 m²/g. When the basic strength of this calcination product was measured, it was found that its maximum basic strength, expressed by pKa determined by the indicator measuring method, was between 26.5 and 27.0. Furthermore, the resulting sodium-supported substance was very strongly basic as shown by the fact that as in Example 1 triphenylmethane having a pKa of 35.0 turned pink from its colorless state.

(2) Two grams of the resulting sodium-supported substance was put in a flask charged with 150 g of 5-vinyl-2-norbornene, and the mixture was stirred at 80° C. for 60 minutes. As in Example 1, all the 5-vinyl-2-norbornene changed to 5-ethylidene-2-norbornene in the reaction mixture. The presence of by-products was not observed.

EXAMPLE 3

(1) A potassium-supported substance containing 8.4% by weight of metallic potassium deposited thereon was obtained in the same way as in Example 1 except that 9.2 g of metallic potassium was used instead of 8.7 g of metallic sodium. The basic strength of the resulting substance was measured by the indicator measuring method. It turned yellow by the adsorption of triphenylmethane having a pKa of 35.0 which turned yellow from its colorless state. This shows that the resulting substance has superstrong basicity with a pKa of at least 35.0.

(2) When 5-vinyl-2-norbornene was isomerized by using the resulting potassium-supported substance in the same way as in Example 1 except that the stirring was carried out at 90° C. for 90 minutes. It was confirmed that all of it changed to 5-ethylidene-2-norbornene.

EXAMPLE 4

Two grams of the sodium-supported substance obtained in Example 2 was taken into a flask under a nitrogen gas atmosphere, and heated to 60° C. under atmospheric pressure. With stirring, 15 g of 4-methylpentene-1 was added. After the lapse of 30 minutes, the reaction mixture was analyzed by gas chromatography (Ucon LB-550, 90 m). All the 4-methylpentene-1 changed to the following compounds.
cis-4-Methylpentene-2: 12.1 mole %
trans-4-Methylpentene-2: 12.0 mole %
2-Methylpentene-2: 75.5 mole %
Others: 0.4 mole %

COMPARATIVE EXAMPLE 1

One hundred grams of alumina (N-613N, a product of Nikki Chemical Co., Ltd.) was treated at 400° C. in air for 4 hours. The resulting powder (40 g; specific surface area 140 m²/g; the maximum basic strength, in pKa by the indicator titration method, was between 15.0 and 17.2) was taken into a 100 ml flask, and heated to 250° C. in a nitrogen atmosphere. With stirring, 4.5 g of metallic sodium was added in small portions over the course of 20 minutes, and the mixture was stirred for 2 hours.

Two grams of the resulting sodium-supported substance was put in a flask charged with 150 g of 5-vinyl-2-norbornene. At 80° C. under atmospheric pressure, the mixture was stirred for 60 minutes. The reaction mixture was analyzed by gas chromatography. It was found that only 37.7 mole % of 5-vinyl-2-norbornene changed to 5-ethylidene-2-norbornene. The rest was recovered as unreacted 5-vinyl-2-norbornene.

COMPARATIVE EXAMPLE 2

Example 4 was repeated except that the sodium-supported substance used in Comparative Example 1 was used. Analysis of the reaction mixture after 30 minutes showed that 47% of 4-methylpentene-1 changed to the following compounds, and the rest was recovered as the unreacted compound.
cis-4-Methylpentene-2: 23.2 mole %
trans-4-Methylpentene-2: 20.5 mole %
2-Methylpentene-2: 56.7 mole %

EXAMPLE 5

Two grams of the sodium-supported substance obtained in Example 1 was fed into a 100 ml autoclave previously charged with 30 ml of n-decane. Diethylamine (7.0 g) and 14.5 g of butadiene were further introduced into the autoclave and reacted at 100° C. under a pressure of 4.7 kg/cm²-G for 2 hours.

Analysis of the reaction product by gas chromatography (PEG-20 M, 2 m) showed that the conversion of diethylamine was 75 mole %, and the product were 73 mole %, out of 75 mole %, of 2-butenyldiethylamine which is a monoadduct of butadiene with diethylamine and 18 mole % of a di-adduct thereof.

COMPARATIVE EXAMPLE 3

Diethylamine and butadiene were subjected to addition reaction in the same way as in Example 5 except using 2 g of a powder obtained by calcining calcium oxide, a commercial reagent, in a nitrogen gas atmosphere at 850° C. for 4 hours (the powder had a specific surface area of 20 m$^2$/g and a maximum base strength, pKa by the indicator titration method, between 26.5 and 27.0). No product was seen to be formed.

EXAMPLE 6

Two grams of the sodium-supported substance obtained in Example 1 was fed into a 100 ml autoclave previously charged with 30 ml of n-decane. Furthermore, 8.5 g of butadiene was introduced and reacted at 50° C. under a pressure of 4.5 kg/cm$^2$-G for 4 hours. Nearly all the butadiene polymerized to a rubbery polymer.

EXAMPLE 7

(1) Preparation of an alkali metal-supported substance

Mg$_{4.5}$Al$_2$(OH)$_{13}$CO$_2$.3.5H$_2$O (Kyoward® 1000, a product of Kyowa Chemical Co., Ltd.) was used as a hydrotalcite compound, and calcined in air at 500° C. for 3 hours. The calcination product had a specific surface area, measured by a B.E.T. one-point method in a Quantasorb specific surface area measuring device made by Quantachrome Company, of 174 m$^2$/g. The specific surface area markedly increased from its original value of 121 m$^2$/g before the calcination. When the basic strength of the calcination product was measured by an indicator measuring method, 4-chloroaniline having a pKa of 26.5 turned pink from its colorless state, and the product showed high basicity.

Twenty-five grams of the calcination product in powder form was taken into a flask, and heated while passing nitrogen at a rate of 0.5 liter/hr. With good stirring, 3.5 g of metallic sodium was added in small portions over the course of about 15 minutes, and the mixture was stirred for about 2 hours to deposit 12% by weight of metallic sodium on the hydrotalcite compound. When the basic strength of the resulting substance was measured by the indicator measuring method, triphenylmethane having a pKa of 35.0 turned yellow from its colorless state, and the substance showed superstrong basicity.

(2) Preparation of a stabilized alkali metal-supported substance

The alkali metal-supported substance prepared in (1) was treated with a gas containing molecular oxygen by using the device shown in FIG. 1.

In FIG. 1, 1 represents a gas flowmeter; 2, a gas desiccator; 3, an agitating motor; 4, a flask to be charged with the alkali metal-supported substance; 5, a mantle heater; 6, a thermocouple; 7,7', cocks; 8, an oxygen analyzer; a, an oxygen gas; b, a nitrogen gas; c, a desiccant; and d, a vent.

The oxygen gas (a) and the nitrogen gas (b) were mixed at 20° C. so as to provide an oxygen concentration of 5.3% by volume. The oxygen-nitrogen gaseous mixture was adjusted to a flow rate of 7 liters/hr by the flowmeter (1), and passed through the desiccator filled with molecular sieves 4A as the desiccant (c) to dry it. The dry gaseous mixture was introduced into the flask charged with the alkali metal-supported substance, conducted into the oxygen analyzer 8 via the cock 7, and discharged (d). The gaseous mixture was heated by the mantle heater 5 (the temperature detecting thermocouple 6) so that the temperature for the stabilization treatment became 125° to 150° C.

Figure 2:
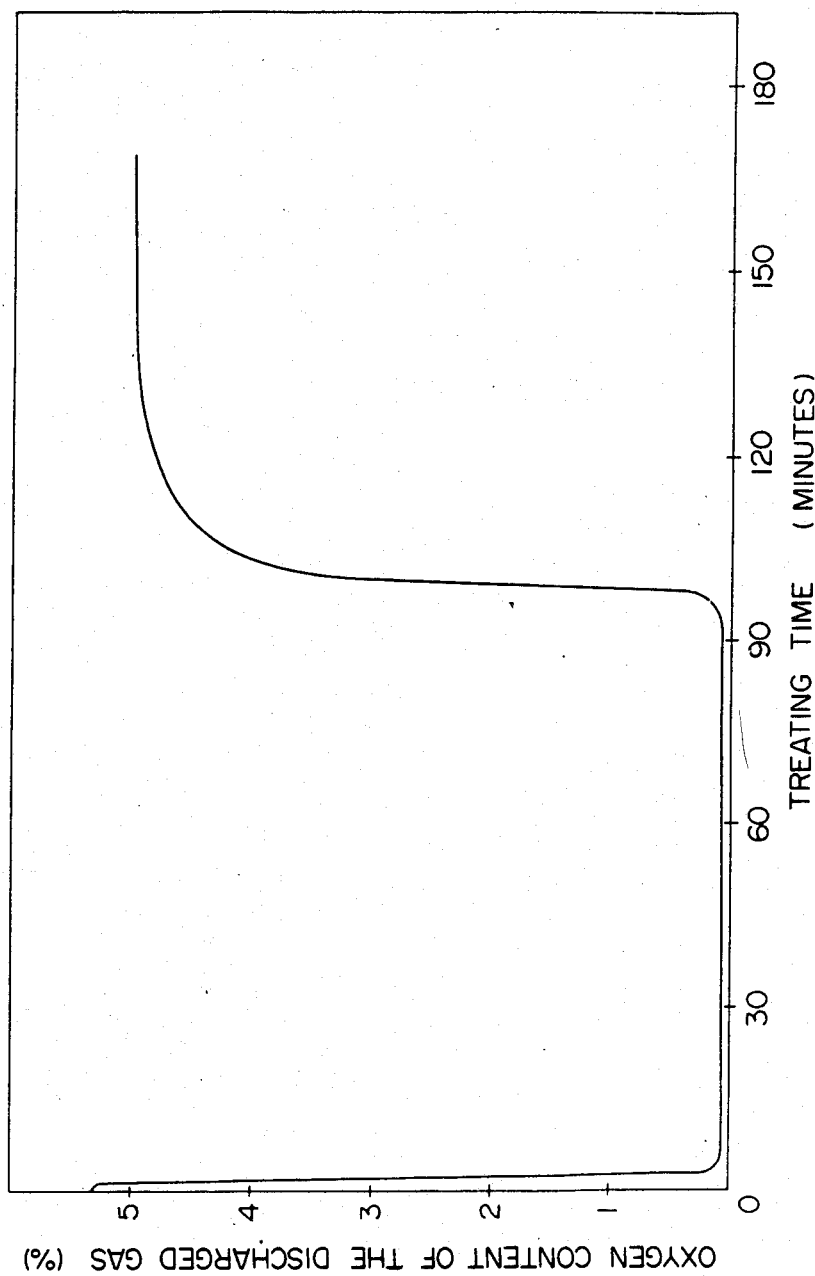
FIG. 2 shows the relation between the treating time and the oxygen content of a discharged gas when an alkali metal-supported substance is treated with a gas containing molecular oxygen by the device of FIG. 1.

The results of analyzing the oxygen concentration of the discharged gas are shown in FIG. 2.

Under the above conditions, the oxygen concentration of the discharged gas instantaneously became nearly 0%, and became equal to the oxygen concentration of the introduced gas in about 1.5 hours. By continuing the oxygen treatment for 150 minutes, a stabilized alkali metal-supported substance was obtained. When the base strength of this substance was examined by the indicator measuring method, triphenylmethane having a pKa of 35.0 turned yellow from its colorless state, and the substance showed superbasicity.

(3) Evaluation of safety

To evaluate the safety of the stabilized alkali metal-supported substance obtained in (2) above, the amount of hydrogen generated at the time of introducing the stabilized substance into water was measured by reading on a gas burette. The amount of hydrogen evolved was as small as 0.7 cc (1.2% of the theoretical amount of hydrogen generated) in a standard condition per gram of the stabilized alkali metal-supported substance. This was a decrease to 1.3% from the amount of hydrogen generated before the stabilization treatment which was 50.4 cc (86.3% of the theoretical amount of hydrogen generated). The results are shown in Table 1.

(4) Evaluation of activity

The activity of the stabilized alkali metal-supported substance used as a catalyst was examined. The stabilized alkali metal-supported substance obtained in (2) in powder form (2.0 g) was put in a flask containing 200 g of 5-vinyl-2-norbornene (VNB), and the mixture was stirred at 100° C. under atmospheric pressure for 60 minutes.

The reaction mixture was analyzed by gas chromatography (filler PEG20 M, 3 m), and it was found that all VNB changed to 5-ethylidene-2-norbornene and no other by-products were observed. The results are shown in Table 1.

TABLE 1

| | pKa | Amount of hydrogen generated (*) [cc (STP)/g-cat] | Yield (%) of 5-ethylidene-2-norbornene |
|---|---|---|---|
| A | >35.0 | 50.4 (86.3) | >99 |
| B | >35.0 | 0.7 (1.2) | >99 |

A: the alkali metal-supported substance
B: the stabilized alkali metal-supported substance
(*): the parenthesized figures show percentages based on the theoretical amount of hydrogen generated

EXAMPLE 8

An alkali metal-supported substance was prepared and stabilized in the same way as in Example 7 except that metallic potassium was used instead of metallic sodium in (1) and the oxygen treating time was changed to 90 minutes in (2). The results are shown in Table 2.

TABLE 2

| | pKa | Amount of hydrogen generated (*) [cc (STP)/g-cat] | Yield (%) of 5-ethylidene-2-norbornene |
|---|---|---|---|
| A | >35.0 | 24.5 (74.2) | >99 |
| B | >35.0 | 1.1 (3.3) | >99 |

In Table 2, A represents an alkali metal-supported substance containing 11.5% by weight of deposited potassium, and B is a stabilized substance obtained by treating A with a gas containing molecular oxygen. (*) has the same meaning as in Table 1.

EXAMPLE 9

Two grams of sodium-supported hydrotalcite prepared in Example 7, (1) and stabilized in Example 7 (2) was put in a container holding 20 g of dehydrated benzaldehyde and 35 g of n-decane as a solvent, and reacted at room temperature for 3 hours. The product was analyzed by gas chromatography (OV-17, 2 m). The conversion of benzaldehyde was 90%, and benzyl benzoate was obtained in a yield of 89%.

EXAMPLE 10

Two grams of the sodium-supported hydrotalcite catalyst prepared in Example 1 was put in a 1-liter flask under a nitrogen atmosphere, and then 400 ml of 3-methyl-1-pentene was added. The reaction temperature was set at 50° C., and 3-methyl-pentene was reacted under atmospheric pressure. The reaction ended within 15 minutes. The contents of the flask were analyzed by gas chromatography (filler Ucon 550, 90 m). The composition of the reaction product was as shown in Table 3.

TABLE 3

| Product | Composition (% by weight) |
|---|---|
| 3-Methyl-1-pentene | 0.5 |
| 3-Methyl-2-pentene (trans) | 31.5 |
| 3-Methyl-2-pentene (cis) | 65.1 |
| Other $C_6$ olefins | 2.2 |
| Others | 0.7 |

EXAMPLE 11

Three grams of the stabilized sodium-supported hydrotalcite catalyst prepared in (1) and (2) of Example 7 was put in a 1-liter flask under a nitrogen atmosphere, and then 400 ml of 3-methyl-1-pentene was added. The reaction temperature was set at 55° C., and 3-methyl-1-pentene was reacted under atmospheric pressure for 30 minutes. After the reaction, the contents were analyzed by gas chromatography (Ucon LB550, 90 m). The composition of the reaction product was as shown in Table 4. After the reaction, 100 ml of water was directly added at a time to the reaction system. But no ignition occurred.

TABLE 4

| Product | Composition (% by weight) |
|---|---|
| 3-Methyl-1-pentene | 0.4 |
| 3-Methyl-2-pentene (trans) | 33.2 |
| 3-Methyl-2-pentene (cis) | 63.8 |
| Other $C_6$ olefins | 1.7 |
| Others | 0.9 |

We claim:

1. An alkali metal-supported substance comprising a calcination product of a hydrotalcite compound represented by the following formula (I)

$$(Mg_{1-x}R_x(OH)_2) \cdot ((CO_3)_{x/2} \cdot mH_2O)$$

wherein R is Al, Cr or Fe, x is a number represented by $0 < x < 0.34$, and m is a number represented by $0 \leq m \leq 5$, and an alkali metal supported on the calcination product.

2. The alkali metal-supported substance of claim 1 wherein the hydrotalcite compound is
   1. $Mg_{0.75}Al_{0.25}(OH)_2 \cdot (CO_3)_{1/8} \cdot 0.5 - 0.652H_2O$,
   2. $Mg_{9/13}Al_{4/13}(OH)_2 \cdot (CO_3)_{2/13} \cdot 7/13H_2O$,
   3. $Mg_{2/3}Al_{1/3}(OH)_2 \cdot (CO_3)_{1/6} \cdot 0.5H_2O$,
   4. $Mg_{2/3}Fe_{1/3}(OH)_2 \cdot (CO_3)_{1/6} \cdot mH_2O$, or
   5. $Mg_{2/3}Cr_{1/3}(OH)_2 \cdot (CO_3)_{1/6}mH_2O$.

3. The alkali metal-supported substance of claim 1 wherein the amount of the alkali metal supported is about 1 to 15% by weight based on the weight of the calcination product of the hydrotalcite compound.

4. The alkali metal-supported substance of claim 1 wherein the alkali metal is sodium or potassium.

5. A stabilized alkali metal-suported substance obtained by subjecting to oxidation treatment with a gas containing molecular oxygen an alkali metal-supported substance comprising a calcination product of a hydrotalcite compound represented by the following formula (I)

$$(Mg_{1-x}R_x(OH)_2) \cdot ((CO_3)_{x/2} \cdot mH_2O)$$

wherein R is Al, Cr or Fe, x is a number represented by $0 < x < 0.34$, and m is a number represented by $0 \leq m \leq 5$, and an alkali metal supported on the calcination product.

6. A stabilized alkali metal-supported substance comprising a calcination product of a hydrotalcite compound represented by the following formula (I)

$$(Mg_{1-x}R_x(OH)_2) \cdot ((CO_3)_{x/2} \cdot mH_2O)$$

wherein R is Al, Cr or Fe, x is a number represented by $0 < x \leq 0.34$, and m is a number represented by $0 \leq m \leq 5$, an alkali metal supported on the calcination product, and an oxide of the alkali metal.

7. The substance of claim 6 wherein the oxide of the alkali metal is formed by the oxidation treatment of a part of the alkali metal supported on the calcination product.

8. The substance of claim 6 wherein the amount of the alkali metal and its oxide is about 1 to 15% by weight as the alkali metal based on the weight of the calcination product.

9. The substance of claim 6 wherein the alkali metal is sodium or potassium.

10. The substance of claim 6 of which maximum basic strength is at least 35 as pKa.

11. The substance of claim 6 which when reacted with water, produces hydrogen gas in an amount of less than amount 15% based on the amount of hydrogen calculated on the assumption that all of the alkali metal and the alkali metal of its oxide contained therein react in accordance with the following formula $$M + H_2O \rightarrow MOH + \tfrac{1}{2}H_2$$

wherein M is an alkali metal.

12. The substance of claim 1, 5 or 6 which is as an isomerization catalyst for olefins.

* * * * *

UNITED STATES PATENT AND TRADEMARK OFFICE
CERTIFICATE OF CORRECTION

PATENT NO. : 4,675,307

DATED : June 23, 1987

INVENTOR(S) : KATSUO TANIGUCHI, ET AL.

It is certified that error appears in the above-identified patent and that said Letters Patent is hereby corrected as shown below:

<u>IN THE CLAIMS</u>

Column 12, line 39, claim 6, delete "$0<X\leq0.34$, insert -- $0<X<0.34$ --.

Signed and Sealed this

Tenth Day of November, 1987

Attest:

DONALD J. QUIGG

Attesting Officer

Commissioner of Patents and Trademarks